United States Patent [19]

Corbin, Jr.

[11] Patent Number: 5,270,287
[45] Date of Patent: Dec. 14, 1993

[54] METHOD FOR DEFOLIATING AND DESICCATING COTTON

[75] Inventor: Billy R. Corbin, Jr., Greenville, Miss.

[73] Assignee: Valent U.S.A. Corporation, Walnut Creek, Calif.

[21] Appl. No.: 963,004

[22] Filed: Oct. 19, 1992

Related U.S. Application Data

[63] Continuation of Ser. No. 605,646, Oct. 30, 1990, abandoned, which is a continuation-in-part of Ser. No. 429,414, Oct. 31, 1989, abandoned.

[51] Int. Cl.⁵ ............................................. A01N 43/34
[52] U.S. Cl. ...................................... 504/167; 504/166
[58] Field of Search ............... 71/69, 74, 75; 504/166, 504/167

[56] References Cited

U.S. PATENT DOCUMENTS

| | | | |
|---|---|---|---|
| 4,484,941 | 11/1984 | Nagano et al. | 71/96 |
| 4,563,535 | 1/1986 | Takemoto | 548/573 |
| 4,640,707 | 2/1987 | Nagano et al. | 71/96 |

FOREIGN PATENT DOCUMENTS

| | | |
|---|---|---|
| 2010827 | 8/1990 | Canada . |
| 2831770 | 1/1979 | Fed. Rep. of Germany . |
| 4023256A1 | 7/1991 | Fed. Rep. of Germany . |
| 4023680A1 | 7/1991 | Fed. Rep. of Germany . |

*Primary Examiner*—Glennon H. Hollrah
*Assistant Examiner*—B. Burn
*Attorney, Agent, or Firm*—Heller, Ehrman, White & McAuliffe

[57] ABSTRACT

N-Aryl tetrahydrophthalimides are useful as cotton defoliants nd desiccants.

6 Claims, No Drawings

METHOD FOR DEFOLIATING AND DESICCATING COTTON

This is a continuation of application Ser. No. 07/605,646 filed Oct. 30, 1990 which is now abandoned is a continuation-in-part of copending Ser. No. 429,414 filed Oct. 31, 1989, now abandoned.

The present invention relates to a method of using N-aryl tetrahydrophthalimides for cotton foliage desiccation and defoliation.

The term "plant-growth regulating agents" generally refers to compounds which advantageously alter the normal growth pattern of plants. In the case of cotton, growth-regulating desiccants and defoliants are particularly desirable to facilitate picking of the cotton bolls. Such agents must desiccate and/or defoliate without harming the cotton bolls and preferably permit the continued growth of the bolls while acting on the foliage. Desirably, the growth regulator will cause the plant to both desiccate and defoliate, thus greatly facilitating picking.

Growth-regulating compounds typically have some degree of herbicidal activity when used in higher concentration, but the converse is rarely true. A number of tetrahydrophthalimides are known to have herbicidal activity, for example, U.S. Pat. Nos. 4,792,605, 4,770,695, 4,640,707 and 4,484,941 disclose such herbicidal compounds.

SUMMARY OF THE INVENTION

The plant growth regulating compounds utilized in the method of the present invention are represented by the formulas I, II and III:

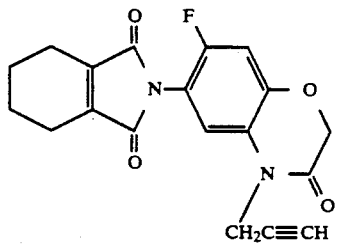

I

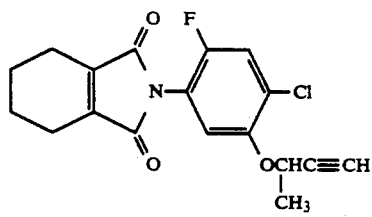

II

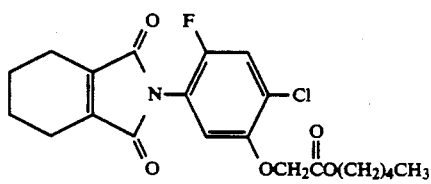

III

The above compound II has an asymmetric carbon atom and hence exists as optical isomers. The respective optical isomers and mixtures thereof are represented by the above formula and are encompassed with the invention.

The compounds of the formulas I, II and III exhibit outstanding cotton desiccating and defoliating activity and do not harm the cotton bolls.

The present invention provides compositions comprising a cotton defoliating and desiccating effective amount of the aforedescribed compounds and an agriculturally acceptable carrier. The invention also provides methods for desiccating and defoliating cotton which comprise treating growing cotton plants with a desiccating and defoliating effective amount of the aforedescribed compounds.

DESCRIPTION OF THE PREFERRED EMBODIMENT

The compounds of the formulas I, II and III are known, and methods of synthesis and formulation are disclosed in U.S. Pat. Nos. 4,792,605, 4,770,695, 4,640,707 and 4,484,941, which are incorporated herein by reference.

The compounds of the formulas (I), (II) and (III) and their salts exhibit cotton plant desiccating and defoliating activity.

Typically, the above compounds are applied at a rate of about 1 to 100 grams, preferably about 5 to 40 grams per acre and are applied directly to the foliage of the cotton plant. Also, although in theory the compounds can be applied undiluted, in actual practice they are generally applied as a composition or formulation comprising an effective amount of the compound(s) and an acceptable carrier. An acceptable carrier (agriculturally acceptable carrier) is one which does not significantly adversely affect the growth-regulating effect achieved by the active compounds, save to dilute it, and does not significantly adversely affect the cotton bolls and is generally nontoxic to the environment in the amounts used. Typically, the composition contains about from 0.1% to 50% by weight of the compound of Formula (I) and/or (II) and/or (III). Conveniently, formulations containing the compound of the formula (I) as active ingredient may be water-dispersible and contain up to about 50% weight/volume of active ingredient. Preferably, formulations containing the compound of the formula (I) or (II) as active ingredient may be flowable fluid concentrates containing up to about 20% weight/volume of active ingredient. Compound (III) is conveniently formulated as an emulsifiable concentrate typically containing up to 10% wt/vol. of Compound (III). Concentrates can also be made having higher concentrations designed for dilution prior to application. The carrier can be a solid, liquid, or aerosol. The final compositions in field use can take the form of granules, powders, dusts, solutions, emulsions, slurries, aerosols, and the like, which may be suitably diluted with water for spraying.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark four, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable conventional aerosol carriers which can be used include conventional aerosol carriers such as halogenated alkanes, etc.

The composition can also preferably contain various promoters and surface-active agents which enhance the rate of transport of the active compound into the plant tissue such as, for example, organic solvents, wetting agents and oils (e.g., paraffin oils) which can increase the ultimate desiccating or defoliating effect. The paraffin oil or wax can be conveniently used with the carrier (for example, water) at concentration of about from 0.25% to 5% by weight of the total composition. The surface-active agent can be anionic, cationic or non-ionic in character. The composition can also contain various compatible adjuvants, stabilizers, conditioners, insecticides, fungicides, and if desired, other compatible cotton growth-regulating compounds.

Plant-growth-regulating tests were made using the following methods.

Five-month old cotton plants were sprayed (spray volume: 10 gal./acre) with the defoliant materials applied as a foliar spray using a tractor boom $CO_2$-sprayer at 5.56 mph, 52 psi pressure, through X-12 hollow cone nozzles (9 nozzles spaced 20" apart, from a height of 18" above the cotton). The air temperature was 56° F., humidity 80%, soil temperature 53° F. (unless otherwise indicated) and the foliage was still damp from dew (8:00 a.m.). The bolls were 70–75% open. The spray was prepared by mixing a formulation concentrate of Compound I, II or III with water containing 1% v/v of a commercial oil spreading agent. A water dispersible granular formulation concentrate or liquid flowable concentrate was used in the case of Compound I and a flowable concentrate was used in the case of Compound II. In the use of Compound III the spray was prepared from an emulsifiable concentrate of Compound III.

TABLE 1

COMPARATIVE COTTON DEFOLIATION

| Test Formulation | | grams a.i./A | % Cotton Defoliation: | |
|---|---|---|---|---|
| | | | 7 Days After Appln. | 17 Days After Appln. |
| 1 | I | 5 | 53 | 72 |
| 2 | I | 10 | 45 | 77 |
| 3 | I | 20 | 42 | 72 |
| 4 | II | 5 | 53 | 77 |
| 5 | II | 10 | 60 | 90 |
| 6 | II | 20 | 58 | 90 |
| 7 | Control A | 91 | 35 | 50 |
| 8 | I | 5 | 40 | 68 |
| | Control A | 45 | | |
| 9 | II | 5 | 55 | 83 |
| | Control A | 45 | | |
| 10 | Control B | 680 | 43 | 75 |
| LSD | | | 15.7 | 15.3 |

1 through 6 were liquids of the active ingredient as a liquid in water containing 1% v/v Agridex (a commercial oil spreading agent).
7 was a control (Control A) of Thidiazuron (a commercial cotton defoliant) in water containing 1% v/v Agridex.
8 and 9 were two active compound mixtures of compounds of the invention and Thidiazuron in water containing 1% v/v Agridex.
10 was a control (Control B) of DEF 6 (a commercial organophosphate cotton defoliant) as an emulsified concentrate.
LSD = the least significant difference between the data points.

TABLE 2

COMPARATIVE COTTON LEAF DESICCATION

| Test Formulation | | grams a.i./A | % Leaf Desiccation: | |
|---|---|---|---|---|
| | | | 7 Days After Appln. | 17 Days After Appln. |
| 1 | I | 5 | 78 | 74 |
| 2 | I | 10 | 78 | 83 |
| 3 | I | 20 | 67 | 82 |
| 4 | II | 5 | 72 | 83 |

TABLE 2-continued

COMPARATIVE COTTON LEAF DESICCATION

| Test Formulation | | grams a.i./A | % Leaf Desiccation: | |
|---|---|---|---|---|
| | | | 7 Days After Appln. | 17 Days After Appln. |
| 5 | II | 10 | 87 | 92 |
| 6 | II | 20 | 87 | 93 |
| 7 | Control A | 91 | 38 | 58 |
| 8 | I | 5 | 60 | 73 |
| | Control A | 45 | | |
| 9 | II | 5 | 82 | 87 |
| | Control A | 45 | | |
| 10 | Control B | 680 | 55 | 78 |
| LSD | | | 19.2 | 13.6 |

TABLE 3

| Test Formulation | | gm a.i./A | 7 days after app. | | 17 days after app. | |
|---|---|---|---|---|---|---|
| | | | # OPEN BOLLS PER 20 | % OPEN BOLLS | # OPEN BOLLS PER 20 | % OPEN BOLLS |
| 1 | I | 5 | 10.6 | 52.8 | 16.1 | 80.6 |
| 2 | I | 10 | 13.0 | 65.0 | 17.0 | 85.0 |
| 3 | I | 20 | 10.0 | 50.0 | 15.7 | 75.0 |
| 4 | II | 5 | 10.7 | 53.3 | 16.7 | 83.3 |
| 5 | II | 10 | 10.3 | 51.7 | 15.3 | 76.7 |
| 6 | II | 20 | 11.0 | 55.0 | 18.7 | 93.3 |
| 7 | A | 91 | 13.0 | 65.0 | 16.3 | 81.7 |
| 8 | I | 5 | 8.7 | 43.3 | 16.0 | 80.0 |
| | A | 45 | | | | |
| 9 | II | 5 | 9.7 | 48.3 | 16.0 | 80.0 |
| | A | 45 | | | | |
| 10 | B | 680 | 9.7 | 48.3 | 15.0 | 75.0 |
| LSD | | | 4.8 | 23.9 | 3.2 | 15.2 |

TABLE 4

COMPARATIVE COTTON YIELD

| Test Formulation | | grams a.i./A | Total Cotton Yield 28 Days After Appl., LB/A |
|---|---|---|---|
| 1 | I | 5 | 1570 |
| 2 | I | 10 | 2181 |
| 3 | I | 20 | 2168 |
| 4 | II | 5 | 2095 |
| 5 | II | 10 | 2132 |
| 6 | II | 20 | 2447 |
| 7 | Control A | 91 | 2628 |
| 8 | I | 5 | 2580 |
| | Control A | 45 | |
| 9 | II | 5 | 2386 |
| | Control A | 45 | |
| 10 | Control B | 680 | 2386 |
| LSD | | | 862 |

A = Thidiazuron, in water containing 1% v/v Agridex.
B = DEF 6, emulsified concentrate, in water.

TABLE 5

COMPARATIVE FIRST CROP PICK

| Test Formulation | | grams a.i./A | % of Total Cotton Crop Harvested On First Pick 34 Days After Appln. |
|---|---|---|---|
| 1 | I | 5 | 58 |
| 2 | I | 10 | 87 |
| 3 | I | 20 | 86 |
| 4 | II | 5 | 88 |
| 5 | II | 10 | 86 |
| 6 | II | 20 | 87 |
| 7 | Control A | 91 | 88 |
| 8 | I | 5 | 89 |
| | Control A | 45 | |
| 9 | II | 5 | 88 |
| | Control A | 45 | |
| 10 | Control B | 680 | 90 |
| LSD | | | 27.2 |

TABLE 6

COMPARATIVE LEAF DESICCATION IN PRESENCE OF MORNING-GLORY
Cotton

| | Formulation | grams a.i./A | % Leaf Desiccation: 2 Days After Appln. | 4 Days After Appln. |
|---|---|---|---|---|
| 11 | Untreated | | 0 | 0 |
| 12 | I | 5 | 60 | 43 |
| 13 | I | 10 | 37 | 60 |
| 14 | I | 20 | 60 | 65 |
| 15 | I | 40 | 60 | 57 |
| 16 | DEF 6 | 510 | 50 | 43 |
| | GRAMOX | 227 | | |
| 17 | SOD | 2721 | 38 | 30 |

| | | | Morning-glory 2 Days After Appln. | 4 Days After Appln. |
|---|---|---|---|---|
| 11 | Untreated | | 0 | 0 |
| 12 | I | 5 | 48 | 45 |
| 13 | I | 10 | 60 | 58 |
| 14 | I | 20 | 60 | 63 |
| 15 | 1 | 40 | 65 | 63 |
| 16 | DEF 6 | 510 | 50 | 50 |
| | GRAMOX | 227 | | |
| 17 | SOD | 2721 | 45 | 50 |

DEF 6 = Commercial organophosphate defoliant.
GRAMOX = Gramoxone, PARAQUAT defoliant formulation sold by ICI. Formulation 16 is in water containing 0.25% v/v of X-77.
SOD = Commercial sodium chlorate. Formulation 17 is in water containing 1% v/v Agridex.
Air temp. 92° F., rel. humidity 69%, soil temperature 99° F.
Formulations 11 through 17 were applied as a spray @20 gal./acre. Formulations 12 through 15 were applied in water containing 1% v/v Agridex.

TABLE 7

COTTON DESICCATION

| | Test Formulation | grams a.i./A | % Cotton Defoliation 7 Days After Appl. | 11 Days After Appl. | 18 Days After Appl. |
|---|---|---|---|---|---|
| 1 | I | 5 | 73 | 84 | 86 |
| 2 | I | 10 | 82 | 86 | 90 |
| 3 | II | 5 | 63 | 86 | 90 |
| 4 | II | 10 | 71 | 88 | 93 |
| 5 | III | 10 | 77 | 85 | 89 |
| 6 | III | 20 | 73 | 83 | 88 |
| 7 | Control | 680 | 81 | 90 | 93 |
| LSD | | | 23 | 13 | 9 |

Formulations 1 and 2 were a water dispersable formulation of the active ingredient (i.e. Compound I) containing 1% b/b Agridex (a commercial oil spreading agent).
Formulations 3 through 6 were liquids of the active ingredient (re Compound II or III) applied in water containing 1% v/v Agridex (a commercial oil spreading agent).
Formulation 7 was a control of DEF-6 (a commercial organophosphate cotton defoliant) as an emulsifiable concentrate.
Formulations 1 through 7 were applied as a foliar spray at 20 gal./acre. Air temperature 56° F., rel. humidity 94%, soil temp. 60° F. About 50 to 65% of harvestable bolls were open.

TABLE 8

COTTON LEAF DESICCATION

| | Test Formulation | grams a.i./A | % Leaf Desiccation 7 Days After Appl. | 11 Days After Appl. | 18 Days After Appl. |
|---|---|---|---|---|---|
| 1 | I | 5 | 85 | 88 | 90 |
| 2 | I | 10 | 92 | 94 | 94 |
| 3 | II | 5 | 75 | 89 | 93 |
| 4 | II | 10 | 85 | 93 | 95 |
| 5 | III | 10 | 90 | 88 | 93 |
| 6 | III | 20 | 94 | 94 | 94 |
| 7 | Control | 680 | 86 | 93 | 94 |
| LSD | | | 16 | 12 | 8 |

TABLE 9

COTTON YIELD

| | Test Formulation | grams a.i./A | Cotton Yield 19 Days After Appl. LB/A |
|---|---|---|---|
| 1 | I | 5 | 2426 |
| 2 | I | 10 | 2799 |
| 3 | II | 5 | 2892 |
| 4 | II | 10 | 3111 |
| 5 | III | 10 | 2332 |
| 6 | III | 20 | 2612 |
| 7 | Control | 680 | 2612 |
| LSD | | | 544 |

Tables 1 and 2 show that at application rates as low as 5 gm. active ingredient/acre of compounds of the invention (I or II), cotton defoliation and leaf desiccation 17 days after application are comparable to that of Control B (at 680 gm/acre) and better than Control A (at 91 gm/acre). At 7 days after application compounds I and II (at 5 gm/acre) are better than Control A and Control B.

Table 3 shows that at application rates as low as 5 gm./acre the compounds of the invention are comparable to both controls (respectively applied at 91 g./acre and 680 g./acre).

Tables 4 and 5 show that Compound II applied at 5 gm/acre is comparable to the controls with respect to total cotton yield and percent of yield harvested on the first pick. Compound I is comparable to the controls when applied at a rate of 10 g./acre.

Table 6 shows comparative leaf desiccation of cotton and morning-glory, a weed which is a problem particularly at the time of cotton harvesting. The twining nature of morning-glory causes it to sprawl up the cotton plants and portions become harvested with the cotton. If the morning-glory is green, it imparts color to the cotton fibers, thus lowering the quality of the harvested product. Table 6 shows that Compound I, applied as low as 5 g./acre, is comparable or better than the controls (formulations 16 and 17) for desiccation of both cotton and morning-glory.

Tables 7, 8 and 9 show that Compound III also gave comparable cotton defoliation, desiccation and yield at 20 g/acre to 680 g/acre of the control desiccant.

I claim:

1. A method for defoliating and desiccating cotton plants comprising the step of applying to the foliage of said plants a defoliating and desiccating effective amount of a composition comprising a compound of the formula I

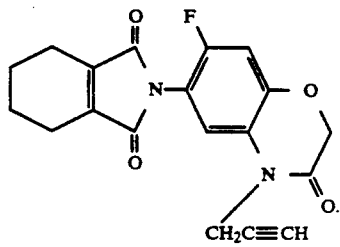

2. A method for defoliating and desiccating cotton plants comprising the step of applying to the foliage of said plants a defoliating and desiccating effective amount of a composition comprising a compound of the formula II

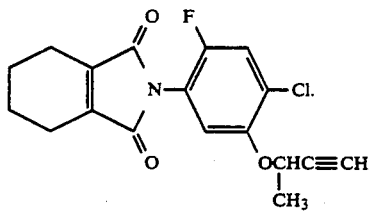

II

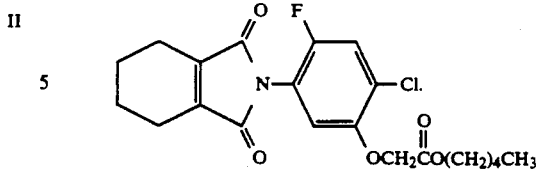

III

3. A method for defoliating and desiccating cotton plants comprising the step of applying to the foliage of said plants a defoliating and desiccating effective amount of a composition comprising a compound of the formula III 4. A method according to claim 1, 2 or 3 wherein said composition comprises a defoliating and desiccating effective amount of said compound.

5. A method according to claim 4 wherein said compound is applied to said plants and their environment at a rate in the range of 1 to 40 grams per acre.

6. A method according to claim 5 wherein said range is 5 to 40 grams per acre.

* * * * *

UNITED STATES PATENT AND TRADEMARK OFFICE
CERTIFICATE OF CORRECTION

PATENT NO. : 5,270,287
DATED : December 14, 1993
INVENTOR(S) : Billy R. Corbin Jr.

It is certified that error appears in the above-indentified patent and that said Letters Patent is hereby corrected as shown below:

On the title page, in the Abstract, line 2, delete "nd" and insert --and--.

Col. 1, line 67 delete "with" and insert --within--.
Col. 5, line 47, delete "b/b" and insert --v/v--.

Signed and Sealed this

Thirty-first Day of May, 1994

Attest:

BRUCE LEHMAN

Attesting Officer        Commissioner of Patents and Trademarks